(12) United States Patent
Zoeller, III

(10) Patent No.: US 7,520,918 B2
(45) Date of Patent: Apr. 21, 2009

(54) METHOD AND SYSTEM FOR IDENTIFYING AND REPAIRING DEFECTIVE CELLS IN A PLUGGED HONEYCOMB STRUCTURE

(75) Inventor: Leon Robert Zoeller, III, Hammondsport, NY (US)

(73) Assignee: Corning Incorporated, Corning, NY (US)

( * ) Notice: Subject to any disclaimer, the term of this patent is extended or adjusted under 35 U.S.C. 154(b) by 548 days.

(21) Appl. No.: 11/303,532

(22) Filed: Dec. 16, 2005

(65) Prior Publication Data

US 2006/0151926 A1 Jul. 13, 2006

Related U.S. Application Data

(60) Provisional application No. 60/638,201, filed on Dec. 21, 2004.

(51) Int. Cl.
*B01D 46/00* (2006.01)
*F01N 3/022* (2006.01)

(52) U.S. Cl. .................. 95/273; 55/282.33; 55/385.3; 55/523; 55/DIG. 5; 55/DIG. 10; 55/DIG. 30; 60/311; 73/40; 264/630; 264/DIG. 48

(58) Field of Classification Search ............. 55/282.2, 55/282.3, 385.3, 523, DIG. 5, DIG. 10, DIG. 30; 95/273; 60/311; 73/40; 264/630, DIG. 48; 362/228, 231, 234
See application file for complete search history.

(56) References Cited

U.S. PATENT DOCUMENTS

| 5,102,434 A | 4/1992 | Hijikata et al. .............. 55/97 |
| 5,317,140 A | 5/1994 | Dunthorn .................... 250/221 |
| 6,627,123 B2* | 9/2003 | Boorom et al. ........ 264/DIG. 48 |
| 6,666,070 B1 | 12/2003 | Hagg et al. .................. 73/38 |
| 6,840,083 B2 | 1/2005 | Hijikata ................... 73/12.01 |
| 2003/0112437 A1* | 6/2003 | Enomoto et al. ............ 356/402 |

FOREIGN PATENT DOCUMENTS

JP  10-123067  5/1998

* cited by examiner

*Primary Examiner*—Jason M Greene
(74) *Attorney, Agent, or Firm*—Matthew B. McNutt

(57) ABSTRACT

A method and system for detecting defects in a plugged honeycomb structure includes forming a sheet of light having a first color across a first end face of the honeycomb structure, generating a first reflected signal from the sheet of light at a location corresponding to a cell containing a defect in the honeycomb structure, illuminating the first end face with an incident light beam having a second color, generating a second reflected signal from the incident light beam, and capturing an image of the first and second reflected signals. After being detected, the defective cells may then be marked or repaired without relocating the plugged honeycomb structure. Apparatus and methods for marking or repairing the defective cell(s) are described.

15 Claims, 12 Drawing Sheets

METHOD AND SYSTEM FOR IDENTIFYING AND REPAIRING DEFECTIVE CELLS IN A PLUGGED HONEYCOMB STRUCTURE

This application claims the benefit of U.S. Provisional Application No. 60/638,201, filed Dec. 12, 2004, entitled "Method and System for Identifying Defective Cells in a Plugged Honeycomb Structure."

FIELD OF THE INVENTION

The invention relates to particulate filters and to methods and systems for detecting defects in particulate filters that may affect the filtration efficiencies of the filters.

BACKGROUND OF THE INVENTION

Wall-flow honeycomb filters are typically used to remove carbonaceous solid particulates from diesel engine exhausts. The honeycomb filter is typically extruded from ceramic precursors mixed with pore forming material. The pore forming material is burned out when the ceramic precursors are fired to produce the hardened ceramic body. FIG. 1 shows a typical wall-flow honeycomb filter 100 having an inlet end face 102, an outlet end face 104, and an array of interconnecting porous walls 106 extending longitudinally from the inlet end face 102 to the outlet end face 104. The interconnecting porous walls 106 define a grid of inlet cells 108 and outlet cells 110. Plugs 112 are inserted at ends of the outlet cells 110 where the outlet cells 110 adjoin the inlet end face 102. Plugs (invisible in the drawing) are also inserted in ends of the inlet cells 108 where the inlet cells 108 adjoin the outlet end face 104. Thus, the outlet cells 110 are open where they adjoin the outlet end face 104, and the inlet cells 110 are open where they adjoin the outlet end face 102.

In a typical cell structure, each inlet cell 108 is bordered on all sides by outlet cells 110 and vice versa. The cells 108, 110 may have a square cross-section as shown. Other cell geometries such as triangle and hexagon are also known. Honeycomb filters having cellular densities between about 10 and 300 cells/in$^2$ (about 1.5 to 46.5 cells/cm$^2$), more typically between about 100 and 200 cells/in$^2$ (about 15.5 to 31 cells/cm$^2$), are considered useful to provide sufficient thin wall surface area in a compact structure. Wall thickness can vary upwards from the minimum dimension providing structural integrity of about 0.002 in. (about 0.05 mm), but are generally less than about 0.060 in. (1.5 mm) to minimize filter volume. A range of between about 0.010 and 0.030 in (about 0.25 and 0.76 mm), e.g., 0.019 in., is most often selected for these materials at the preferred cellular densities.

The honeycomb filter 100 may be installed in a housing, which may then be inserted into the exhaust system of a vehicle equipped with a diesel engine. In operation, diesel exhaust directed at the inlet face 102 of the honeycomb filter 100 flows into the inlet cells 108. The interconnected porous walls 106 are provided with an internal interconnected open porosity that allows the exhaust to pass from the inlet cells 108 to the outlet cells 110 while restraining a desired portion of the solid particulates in the exhaust. The filtered exhaust exits the filter through the outlet cells 110.

Filtration efficiencies up to and in excess of 90% by weight of the diesel exhaust particulates can be achieved with honeycomb filters such as described above. However, the filtration efficiency achievable can be dramatically reduced if there are leaks in the honeycomb filter due to defects, such as holes and cracks, in the interconnecting porous walls and plugs in the filter. Thus in the production of honeycomb filters for diesel particulate filtration, it is customary to test the honeycomb filters for leaks. Defective cells producing leaks are identified and repaired. The test may be repeated until it is ascertained that there are no leaks from the honeycomb filter. The test may be performed while the honeycomb structure is still green or after firing the honeycomb structure. In general, it is easier to repair defects while the honeycomb structure is still green.

One prior-art method for identifying defective cells in a plugged honeycomb filter involves taping a clear film to one end of the honeycomb structure and pouring graphite into the opposite end of the honeycomb structure while rotating the honeycomb structure about two axes. Defective cells having voids within their walls or plugs allow the graphite particles to pass through and are detected by presence of the graphite particles on the clear film. Variations of this method include replacing the graphite particles with other particles, such as micro glass and plastic beads.

Another prior-art method for identifying defective cells in a plugged honeycomb filter is disclosed in U.S. Pat. No. 5,102,434 (Hijikata et al.). In this method, a gas containing solid particulates, such as carbon soot, is flowed under pressure into one end of the honeycomb structure. A gas-permeable screen is placed adjacent the opposite end of the honeycomb structure to collect solid particulates from the gas flowing out of the honeycomb structure. The screen is inspected for patterns differing from the defect-free structure.

The methods described above require fired plugged honeycomb structures and do not reliably detect defects in cases where the solid particulates are too big to flow through the defects. In cases where graphite particles are used for testing, small amounts of graphite particles remain inside the honeycomb structure after testing, which can interfere with the downstream processing of the honeycomb structure, such as catalyst coating process. Further, additional steps are required to clean and remove the solid particulates used for testing from the filter.

Another prior-art method for identifying defective cells in a plugged honeycomb filter involves securing a heat sensitive film (liquid crystal) to one end of a honeycomb filter. The heat sensitive film is initially heated. Cold air is blown from the opposite end of the filter to the film. The air that passes uninhibited through the voids and cracks within the walls of the filter cools the films at the location of the defective cells. This method is suitable for identifying defective cells in green plugged honeycomb filter.

SUMMARY OF THE INVENTION

In one aspect, the invention is a method of identifying defective cells in a plugged honeycomb structure which comprises forming a sheet of light having a first color across a first end face of the honeycomb structure, generating a first reflected signal from the sheet of light at a location corresponding to a cell containing a defect in the honeycomb structure, illuminating the first end face with an incident light beam having a second color, generating a second reflected signal from the incident light beam, and capturing an image of the first and second reflected signals.

In another aspect, the invention is a system for identifying defective cells in a plugged honeycomb structure which comprises a holder which supports the honeycomb structure, a first light source which forms a sheet of light having a first color across a first end face of the honeycomb structure, a second light source which illuminates the first end face with an incident light beam having a second color, a gas source which directs a gaseous material at a second end face of the honeycomb structure, and an imaging device which captures an image of reflected signals produced from the sheet of light and the incident light beam.

In yet another aspect, the invention is an illuminator which comprises a plurality of first light sources generating beams having a first profile and a plurality of second light sources generating beams having a second profile, wherein the first and second light sources are arranged such that the beams having the first profile overlap with the beams having the second profile to produce a uniform sheet of light.

In yet a further aspect, the invention is method of manufacturing a plugged honeycomb structure, comprising the steps of positioning the plugged honeycomb structure in a holder, imaging a defective cell of the plugged honeycomb structure, generating a location coordinate of the defective cell of the plugged honeycomb structure, moving to the location coordinate, and marking or repairing the defective cell without relocating the plugged honeycomb structure from the holder.

Other features and advantages of the invention will be apparent from the following description and the appended claims.

DETAILED DESCRIPTION OF THE INVENTION

The invention will now be described in detail with reference to a few preferred embodiments, as illustrated in accompanying drawings. In the following description, numerous specific details are set forth in order to provide a thorough understanding of the invention. However, it will be apparent to one skilled in the art that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

Embodiments of the invention provide a method and a system for identifying defective cells in a plugged honeycomb structure. The defective cells identified are those that if not repaired can produce leaks from the plugged honeycomb structure. In general, the invention involves forming a sheet of light having a first color across a first end face of the honeycomb structure and illuminating the first end face with a light having a second color. A gaseous material is flowed into the honeycomb structure through a second end face of the honeycomb structure. Gaseous material (gas with suspended particles) emerge at the first end face of the honeycomb structure if there are defects in the honeycomb structure that can produce leaks. The defects may be in the cell walls or plugs. The particles, upon emerging from the first end face, intersect the sheet of light, producing a first reflected signal having the first color. In addition, the light illuminating the first end face reflects off the first end face, producing a second reflected signal having the second color. Both the first and second reflected signals are detected and used to form an image from which the size and position of the defects producing the leaks can be determined. The cells containing the identified defects may be repaired. The method is particularly effective in detecting defects in a "green" plugged honeycomb structure. The walls in a "fired" plugged honeycomb structure are porous, making testing using this method somewhat more difficult because of the generally higher base flows of gaseous material through the structure.

Figure 1:
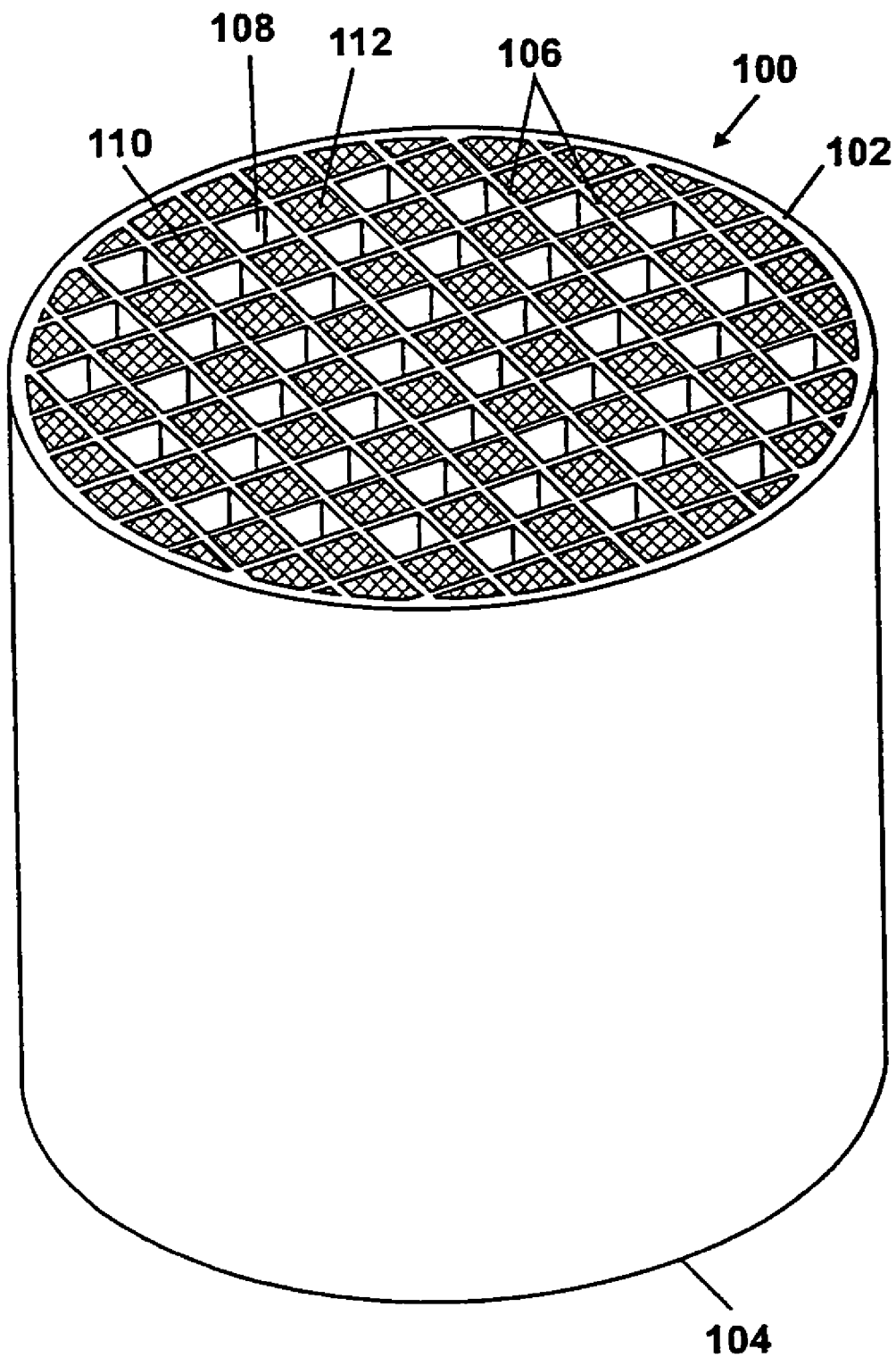
FIG. 1 shows a prior-art honeycomb filter.
Figure 2:
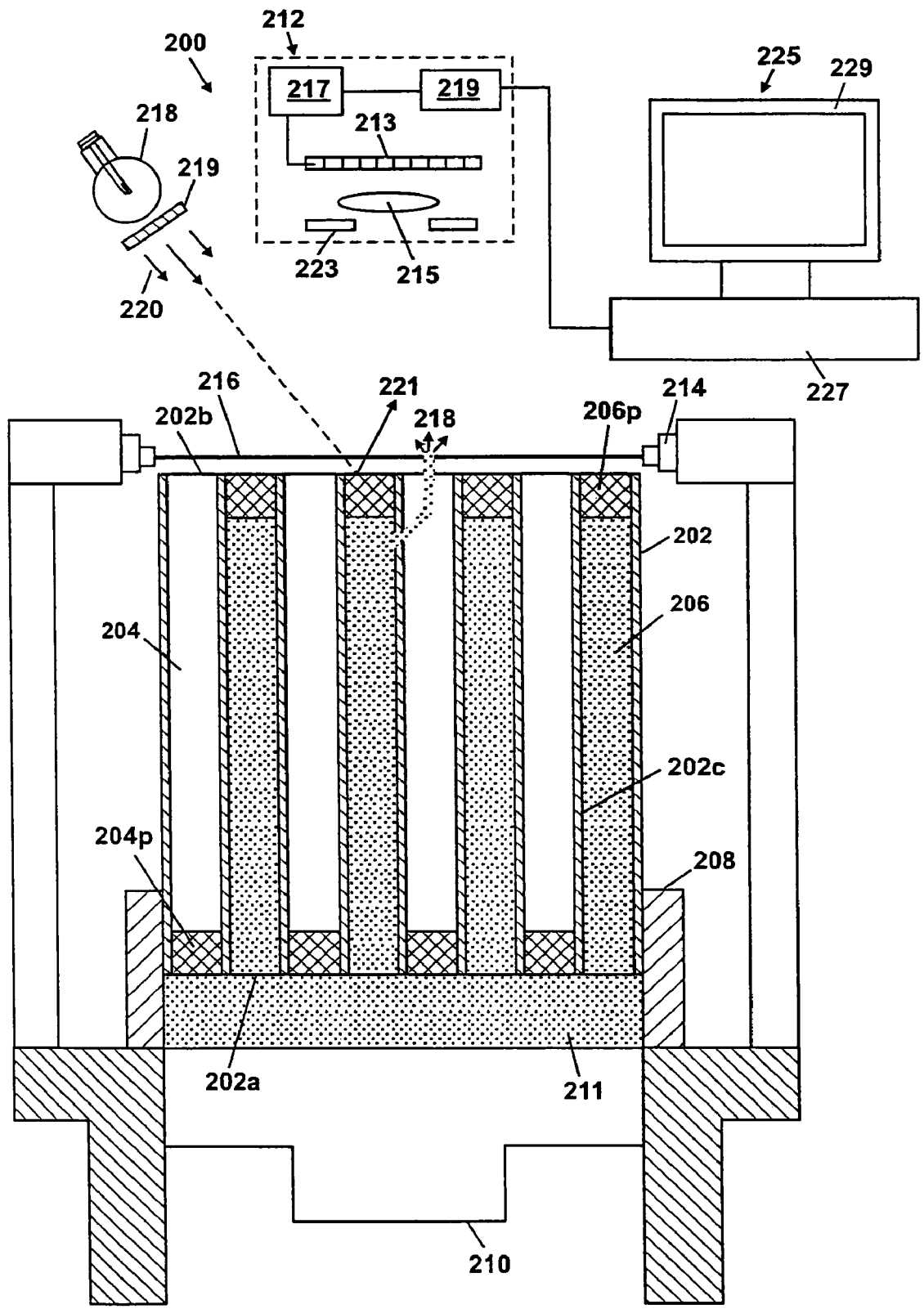
FIG. 2 illustrates a system for identifying defective cells in a honeycomb structure according to one embodiment of the invention.

FIG. 2 is a schematic of a system 200 for identifying defective cells in a plugged honeycomb structure 202 according to one embodiment of the invention. The plugged honeycomb structure 202 may be extruded from ceramic precursors, such as cordierite or silicon carbide, mixed with pore formers, such as graphite, or cellulosic materials. The ceramic precursors can be fired to burn out the pore formers and/or cellulosic materials and form a solid ceramic body. The solid ceramic body can be inserted in a housing and used as a solid particulate filter in, for example, the exhaust system of a diesel engine. The honeycomb structure 202 has end faces 202a, 202b and interior walls 202c extending between the end faces 202a, 202b. The walls 202c define cells 204, 206. Plugs 204p, 206p are inserted in the ends of the cells 204 adjoining the end face 202a and the ends of the cells 206 adjoining the end face 202b, respectively. The ends of the cells 204 adjoining the end face 202b and the ends of the cells 206 adjoining the end face 202a are left unplugged. The material of the plugs 204p, 206p may be a mixture of ceramic material with a binder and a plasticizer. The walls 202c are porous after firing. The thickness and porosity of the walls 202c after firing are such that the structural integrity of the honeycomb structure 202 is not compromised. For diesel exhaust filtration, the porous walls 202c may incorporate pores having mean diameters in the range of 1 to 60 µm, more preferably in a range from 10 to 50 µm. The system 200 includes a holder 208 in which the honeycomb structure 202 is supported.

The system 200 includes a gas source 210 positioned below the end face 202a of the honeycomb structure 202. In operation, the gas source 210 directs a gaseous material 211 at the end face 202a of the honeycomb structure 202. The gaseous material 211 enters the honeycomb structure 202 through the open ends of the cells 206. The gaseous material 211 may also enter the honeycomb structure 202 through any of the plugs 204p if there are defects in them that permit such entry. The gaseous material 211 may be a gas, such as air or inert gas, or vapor generated from a solid or liquid material. In the latter case, the gas source 210 may be a device capable of generating vapors, e.g., a humidifier or any kind of particle generator or any suitable means for forming a gas material (a gas flow with some particle therein). The gas source 211 may also include a blower device such as a fan for directing the gaseous material 211 at the end face 202a. Preferably, the gaseous material 211 does not interact with the material of the honeycomb structure 202. If there are defects in the honeycomb structure 202 that can produce leaks, the gaseous material 211 entering the honeycomb structure 202 will emerge at the end face 202b. The cells through which the gaseous material 211 emerges at the end face 202b are the defective cells.

The system 200 includes an imaging system 212 positioned above the end face 202b. The imaging system 212 generates images using light reflected from an object, such as the honeycomb structure 202. As an example, the imaging system 212 may be a camera or camcorder. In one embodiment, the imaging system includes a light sensor 213 which is capable of sensing at least two different light colors. In one embodiment, the light colors are selected from the group consisting of red, green, and blue. In one embodiment, the light sensor 213 is a CCD ("charge-coupled device") sensor. However, the invention is not limited to use of a CCD sensor as the light sensor. A CMOS sensor or other solid-state sensor may also be used. In the embodiment where the light sensor 213 is a CCD sensor, it includes an array of light-sensitive cells called photosites. The photosites are made of silicon. The photosites emit electrons when light impinges on them. The brighter the light impinging on them, the higher the number of electrons emitted. To allow the CCD sensor to detect colors, each photosite has an associated color filter, which may be red, green, or blue. The photosite can only detect the brightness of the light that matches its color filter.

The imaging system 212 further includes one or more lenses 215 for focusing light from an object, such as the honeycomb structure 202, on the light sensor 213. The imaging system 212 may also include a zooming feature, which may be achieved optically through the use of zoom lenses or digitally. The imaging system 212 may also include a processor 217 that controls operation of the imaging system 212. The processor 217 processes the information collected by the light sensor 213 into image files and stores the image files on memory 219. The processor 217 may support various types of image file formats, such as TIFF and JPEG. The imaging system 212 may include a built-in screen (not shown) for displaying the image files. The imaging system 212 may further include a shutter, represented by 223, for controlling entry of light into the system. The imaging system 212 may be coupled to a computer system 225 (not drawn to scale). The computer system 225 may include a processor 227 and video monitor 229 and other peripheral devices necessary for interacting with the system, such as a keyboard and mouse. These peripheral devices are well known in the art and will not be discussed further. The image files stored on memory 219 can be transferred to the processor 227 for further processing. The image files may also be displayed on the video monitor 229.

The system 200 includes a first illuminator 214 which projects a sheet of light 216 just above the end face 202b of the honeycomb structure 202. In one embodiment, the first illuminator 214 may include several first light sources to generate a uniform sheet of light across the end face 202b of the honeycomb structure 202. The sheet of light 216 has a first color, which may be selected from the group consisting of red, blue, and green. For example, the sheet of light 216 may have a red color. Since the sheet of light 216 is positioned just above the end face 202b, gaseous particles emerging at the end face 202b (as a result of a defect in the honeycomb structure 202) would pass through the sheet of light 216, scattering the sheet of light 216 at the locations where they pass through the sheet of light 216. For illustration purposes, the light reflected off the particles is represented by arrow 218. If the shutter 223 of the imaging system 212 is open, the reflected light 218 will impinge on the light sensor 213. If the light sensor 213 is a CCD sensor, the reflected light 218 will impinge on the photosites. The larger the size of the defect, the more the amount of gaseous particles released from the defective cell. The more the amount of gaseous particles released from the defective cell, the larger the number of photosites impinged by the light reflected from the gaseous particles or the higher the number of electrons emitted by the photosites impinged. Thus, an image produced from the reflected light 218 can serve as a measure of the size of the defect from which the particles emerged. This image may be referred to as "defect image," and the reflected light from which the defect image is produced may be referred to as "defect signal."

The system 200 includes a second illuminator 218, which is positioned such that it illuminates the end face 202b of the honeycomb structure 202 with light 220. The light 220 has a color selected from the group consisting of red, green, and blue. The second illuminator 218 may include an optical filter 219 which controls the color of the light 220 reaching the end face 202b of the honeycomb structure 202. The color of the light 220 is selected to be different from the color of the sheet of light 216. For example, if the sheet of light 216 has a red color, then the light 200 would have a blue or green color. This allows separation of the information collected using the first illuminator 214 from the information collected using the second illuminator 218. The light 220 impinging on the end face 202b is reflected off the end face 202b, as shown by arrow 221. If the shutter 223 of the imaging system 212 is open, the reflected light 221 impinges on the light sensor 213 in the imaging system 212, thereby causing an image of the end face 202b to be captured. This image may be referred to as "surface image," and the reflected light from which the surface image is produced may be referred to as "surface signal." The surface image shows the cell configuration at the end face 202b.

In the system described above, the defect signals can be adjusted independently of the surface signals since the light sources used in producing them are separate. This allows the sensitivity of the system to be adjustable and more easily maintained as a standard. The defect image, obtained using the first illuminator 214, shows the sizes and locations of defects in the honeycomb structure 202 producing leaks, and the surface image, obtained using the second illuminator 218, shows the cell configuration at the end face 202b. The surface image may be captured at the same time that the defect image is captured to produce a single image having two color components. As an example, if the first illuminator 214 produces a red color light and the second illuminator 218 produces a blue color light (which may or may not be achieved through the use of filters), the single image would have a red color component and a blue color component. The red color component provides information about the size and location of the defects in the honeycomb structure 202, and the blue color component provides information about the cell configuration of the end face 202b. Using this single image, the cells containing the defects can be identified and appropriate actions can be taken to repair the defective cells. It is also possible to capture the surface image and the defect image at different times by controlling when the illuminators 214, 218 are turned on. These images may be separately examined to identify the defective cells. Alternatively, a post-processing application may be used to combine the surface and defect images to produce a single image from which the defective cells can be identified.

Figure 3A:
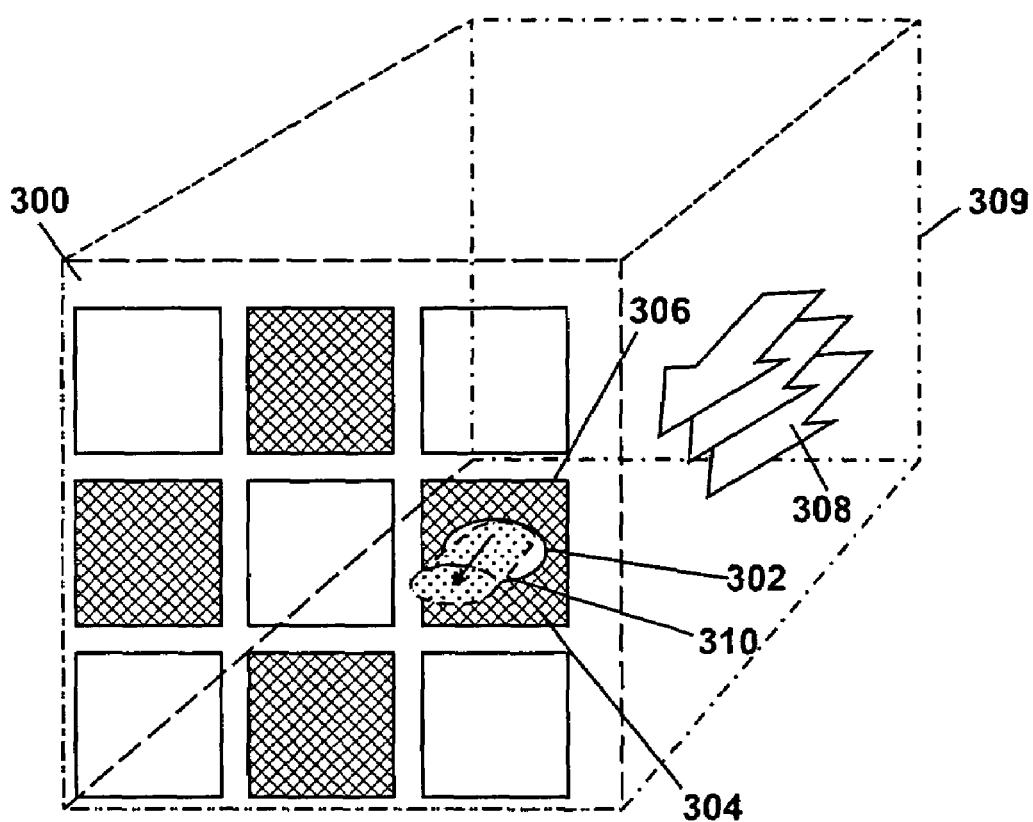
FIG. 3A shows an end face of a honeycomb structure and gaseous particles emerging from a defect in the end face according to one embodiment of the invention.
Figure 3C:
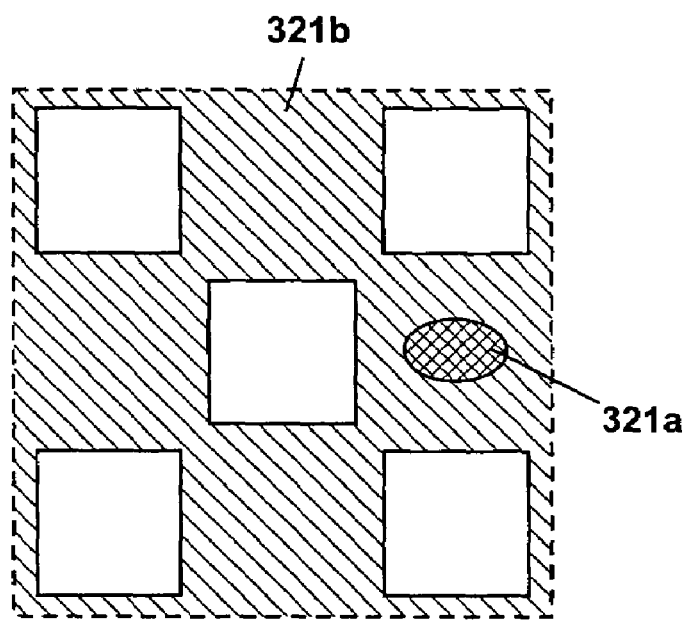
FIG. 3C illustrates an image formed from the reflected light shown in FIG. 3B.
Figure 3B:
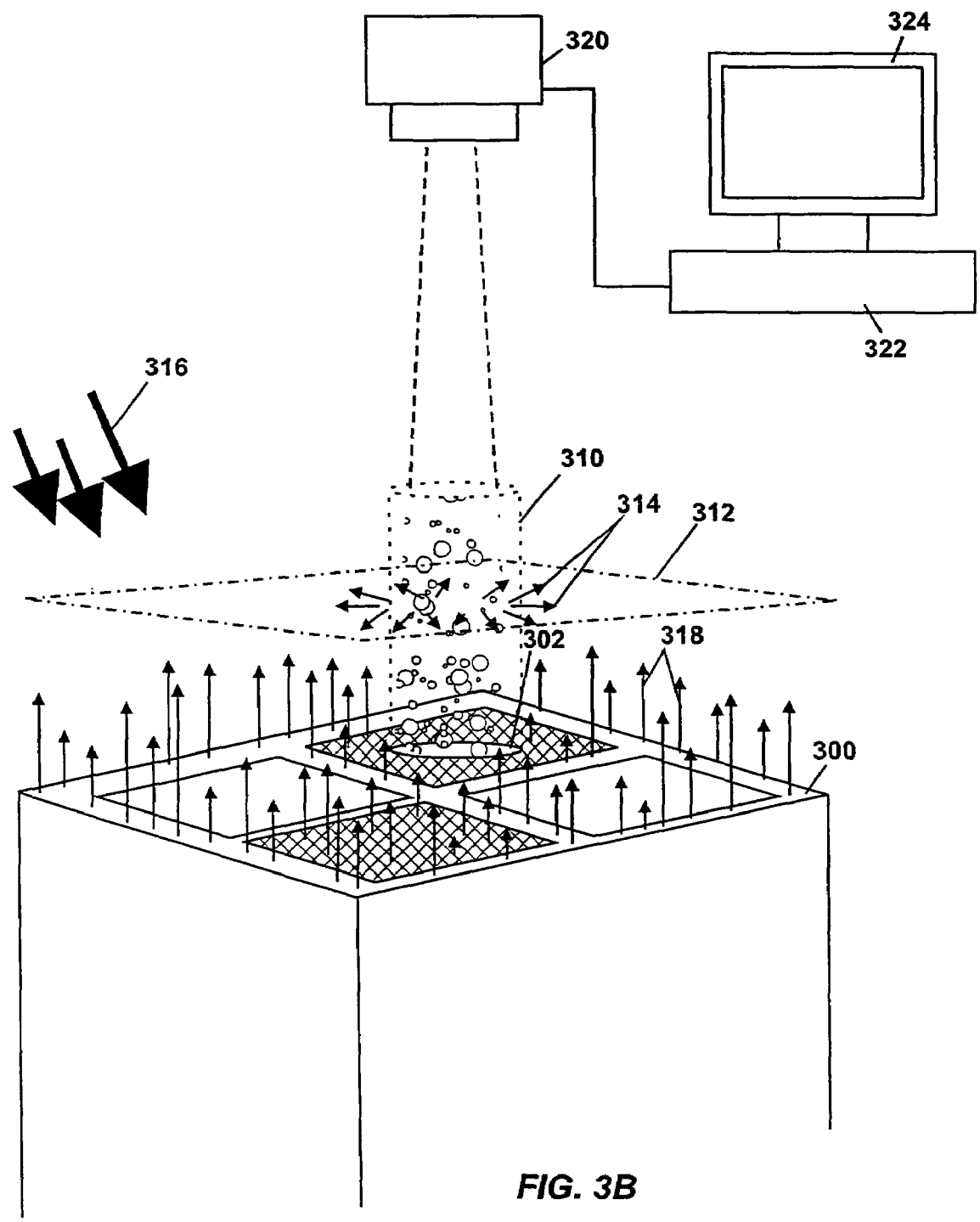
FIG. 3B shows light reflected from the end face and gaseous particles shown in FIG. 3A according to one embodiment of the invention.

For illustration purposes, FIG. 3A shows an enlarged, partial view of an end face 300 of a honeycomb structure having a defect 302. In the example shown, the defect 302 appears in the end face 300, but this may not necessarily be the case in all honeycomb structures. That is, defects could appear anywhere in the honeycomb structure, for example, in the interior of the honeycomb structure. However, it is convenient for illustration purposes to show the defect in the end face 300. The defect 302 is located in a plug 304 formed in a cell 306. In FIG. 3A, a gaseous material 308 is flowing into the honeycomb structure through the opposite end face 309 of the honeycomb structure. Also, particles 310 of the gaseous material 308 are emerging at the end face 300 through the defect 302. FIG. 3B shows the particles 310 intersecting a sheet of light 312 above the end face 300 and producing reflected light 314 as a result. Also, reflected light 318 is produced as a result of light 316 impinging on the end face 300.

Assuming that the color of the reflected light 314 is red and the color of the reflected light 318 is blue, then an imaging system 320 positioned above the end face 300 would generate an image consisting of red and blue components—the green color is unused. FIG. 3C shows an example of such an image, where the red component is represented by the cross-hatched region 321a and the blue component is represented by the hatched region 321b. The red component 321a gives information about the size and location of the defect (302 in FIG. 3B) while the blue component 321b gives information about the cell configuration of the end face (300 in FIG. 3B). The red and blue components combined together provide information about the size of the defect and the cell containing the defect. Returning to FIG. 3B, the image obtained by the imaging system 320 could be further processed by a processor 322. For example, the processor 322 could generate actual coordinates of the cell containing the defect 302 and size of the defect 302 from the image and display such information on a monitor 324. Using the coordinates of the defective cell, the processor 322 may further control a robot device to mark and/or repair the defective cell in the honeycomb structure. Alternatively, such marking and repairing may be accomplished manually.

Figure 4:
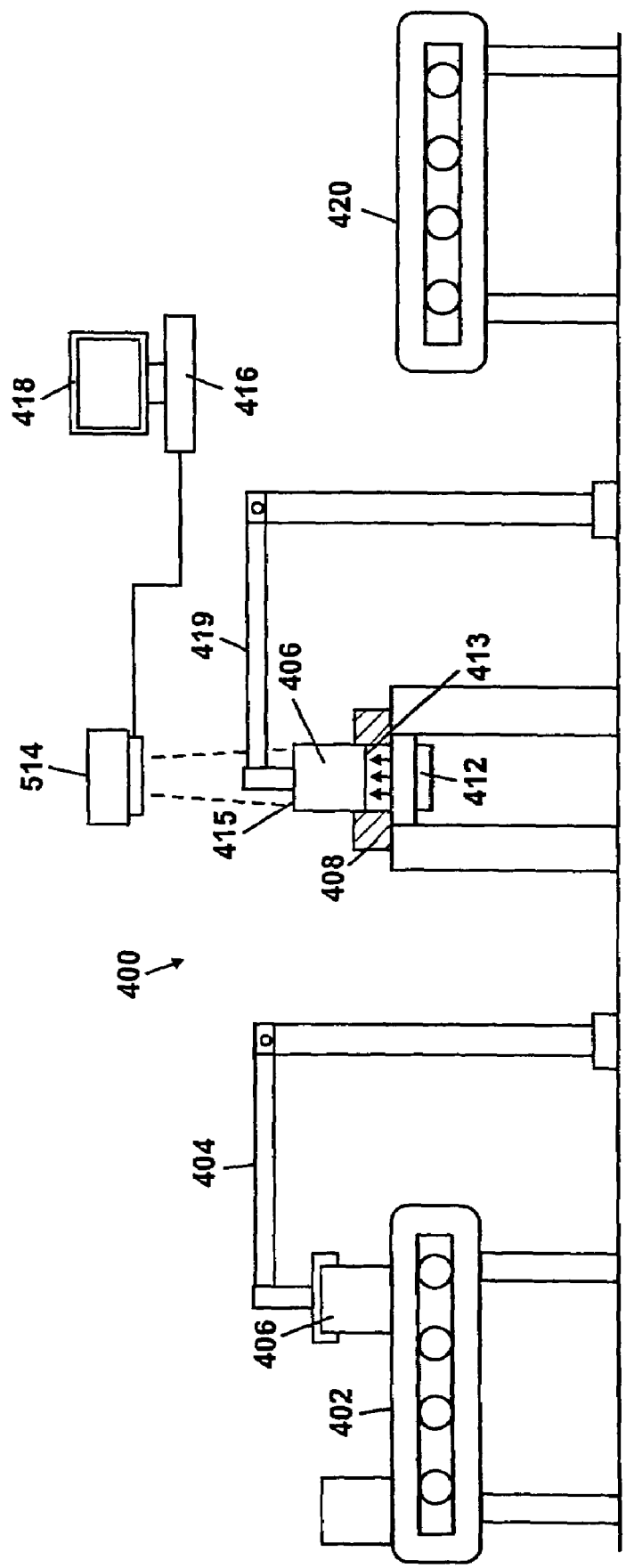
FIG. 4 illustrates an automated system for identifying defective cells in plugged honeycomb structures according to one embodiment of the invention.

FIG. 4 illustrates an automated system 400 for detecting defects in a honeycomb structure according to one embodiment of the invention. The automated system 400 includes a conveyor preferably having a conveyor belt 402 that transports honeycomb structures to a robot including a robotic arm 404. The robotic arm 404 picks a honeycomb structure 406 from the conveyor belt 402 and positions the honeycomb structure 406 in a holder 408 such that an inspection may take place to determine the coordinate locations of any defective cells. A gas source 412 is positioned below the holder 408, and an imaging system 414 is positioned above the holder 408. The gas source 412 directs gaseous material containing particulates at an end face 413 of the honeycomb structure 406, and the imaging system 414 captures an image of reflected light from particles emerging at the end face 415 of the honeycomb structure 406. The image captured is sent to a processor 416, which generates coordinates of defective cells, if any, and sizes of defects, if any, from the image. A visual representation of the image may be displayed on the monitor 418.

Figure 9:
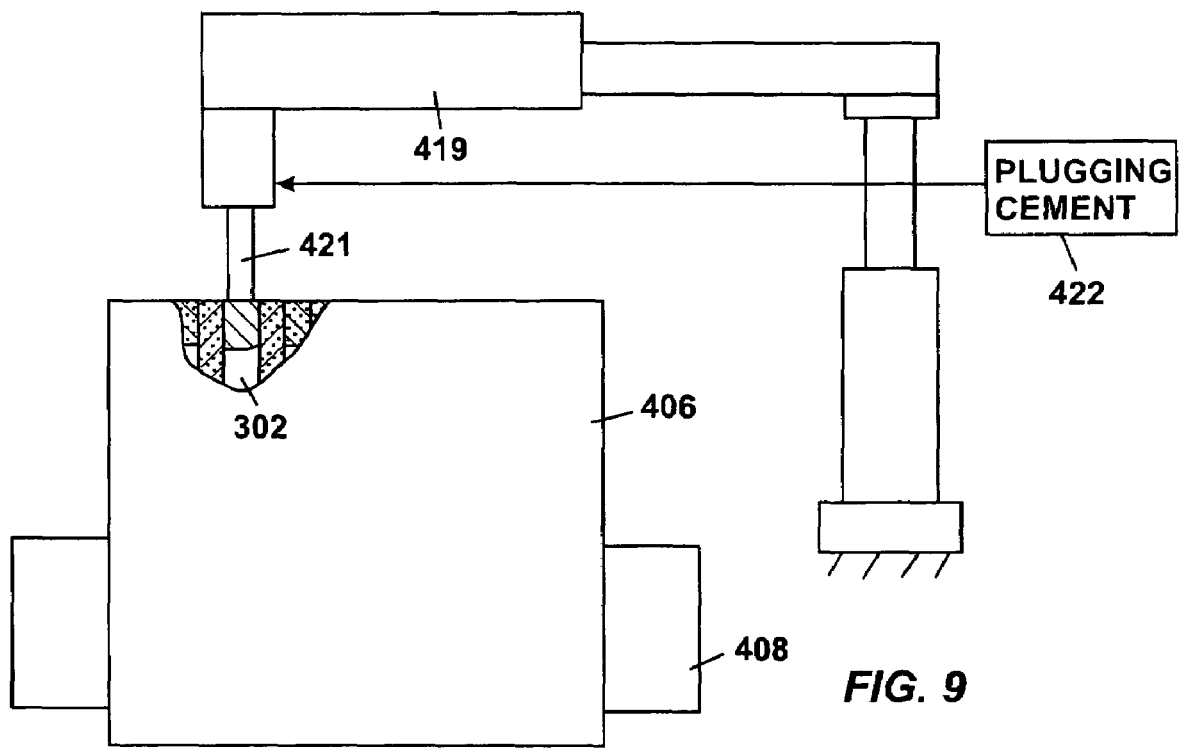
FIG. 9 shows a side view of an apparatus illustrating repair of a defective cell by a metering head according to an embodiment of the invention.

The processor 416 may use the coordinates to control a robot arm 419 to mark the defective cells in the honeycomb structure 506 while the structure is already positioned and without relocating the structure from the holder 408 of the inspection apparatus. Optionally, as shown in FIG. 9, the processor 416 may also control the robot arm 419 to repair the defective cells in the honeycomb structure 406 prior to relocation of the structure. The repair is preferably accomplished by moving a metering head 421 by a robot capable of X-Y-Z directional movement to the coordinate position of the defective cell(s) 302 of the honeycomb structure 406 and facilitates the repair by dispensing from the metering head 421, an amount of plugging cement to repair, i.e., form a plug in the defective cell. The metering head 421 is preferably connected to a supply of plugging cement 422 which may be remotely located or positioned near the metering head. Preferably, the robot arm 419 moves the metering head into the desired position above the defective cell of the structure 406. Optionally, the metering head may be attached to, and moved by, a separate robot. The robot arm 419 may pick up and position the honeycomb structure 406 on another conveyor including a conveyor belt 420 after marking and/or repairing the defects, allowing another honeycomb structure to be processed.

Figure 10:
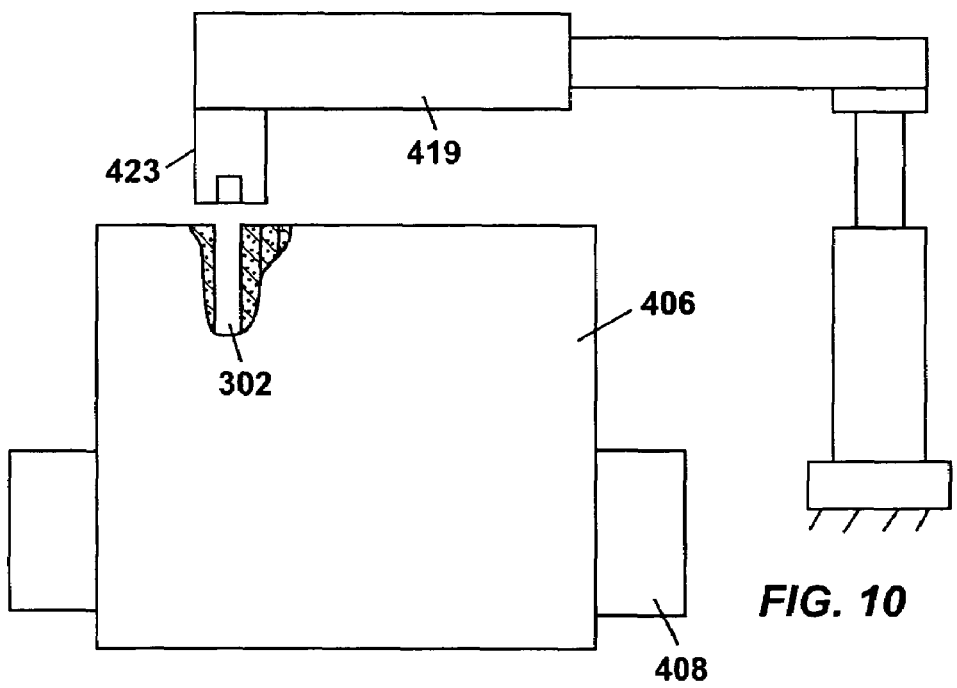
FIG. 10 shows a side view of an apparatus illustrating marking of a defective cell by a marking implement according to an embodiment of the invention.

The marking, if performed, may be accomplished by a suitable marking implement 423, such as an ink jet head, for example. The marking implement 423 is positioned, by a robotic arm 419, at the X-Y-Z coordinate location of the defective cell 302 of the honeycomb structure 406 as shown in FIG. 10. The marking implement 423 then marks the defective cell by spraying ink on the ends of the walls surrounding the cells. Optionally, the marking may be accomplished by a suitable pen or paint brush. Any suitable marking implement may be used. In any event, the marking is accomplished by the robot arm 419 or a separate robot arm marking the defective cell with the implement such that it is identified and may be repaired later at another station.

The invention typically provides the following advantages. Use of solid particulates such as graphite for testing is avoided. This eliminates the need to clean the honeycomb structure after testing. The testing can be accomplished quickly, e.g. in less than one minute. The added step of rotating the honeycomb structure is eliminated. The testing is environmentally friendly in that it does not require the use of toxic materials. The testing is repeatable. The testing requires little human intervention. The testing can be easily automated. The system described above allows the defect signal (produced by defects in the honeycomb structure) to be decoupled from the surface signal (produced by the end face of the honeycomb structure). Therefore, the quality of the defect signal can be adjusted independently of the quality of the surface signal, which results in a system with enhanced sensitivity and robustness.

Figure 5A:
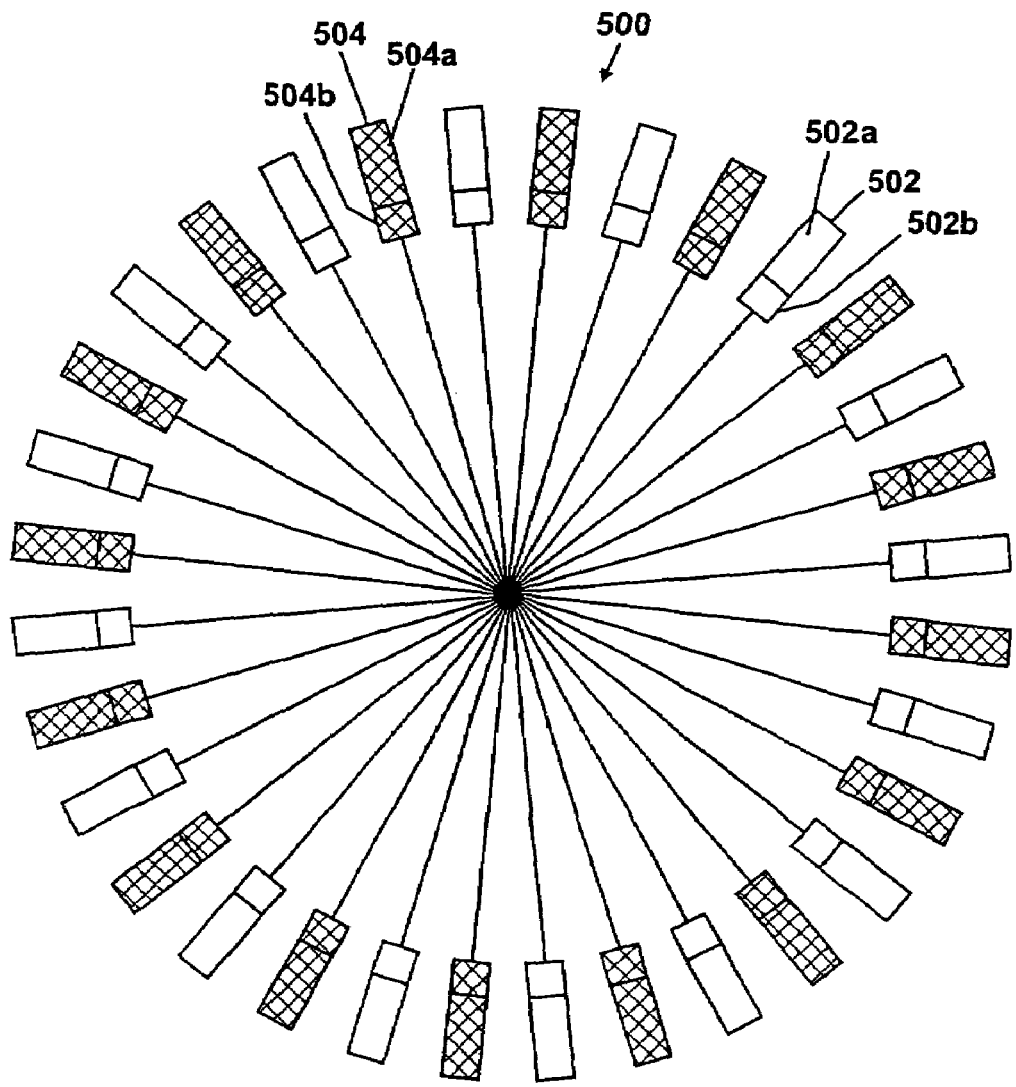
FIG. 5A illustrates an illuminator for forming a uniform sheet of light according to an embodiment of the invention.

FIG. 5A shows an illuminator 500 which produces a uniform sheet of light according to an embodiment of the invention. The term "uniform sheet of light" generally means that the maximum variation in light intensity across the sheet of light is less than 10%, preferably less than 5%, more preferably less than 3%. The illuminator 500 may be used wherever it is desired to provide equal illumination energy across a surface of a substrate. The illuminator 500 may be used to illuminate fluid, such as air, gas, vapor, mist, and steam, emerging from the surface of the substrate. When the fluid passes through the sheet of light, particles in the fluid reflects light in all directions. A light sensitive device, such as a camera or human eye, viewing perpendicular to the sheet of light would be able to see the particles under illumination. The illuminator 500 together with a suitable imaging system allows the dynamics and size of these particles to be measured. One use of the illuminator 500 is in the system described above for identifying defective cells in a plugged honeycomb structure. For example, the illuminator 500 could be used as the first illuminator (214 in FIG. 2) to provide a uniform sheet of light across the end face (202b in FIG. 2) of the honeycomb structure (202 in FIG. 2). Equal illumination provided across the end face of the honeycomb structure would make it possible to determine not just the position of a leak in the honeycomb structure but also the magnitude of the leak. The amount of light reflected as a result of particles from the leak hitting the uniform sheet of light provides a measure of the magnitude of the leak.

The illuminator 500 includes a plurality of first light sources 502 and a plurality of second light sources 504. In one embodiment, the light sources 502, 504 are arranged in a ring pattern. However, the invention is not limited to arranging the light sources 502, 504 in a ring pattern. Other suitable shapes, which may be selected to match the surface area to be illuminated, may also be used. In one embodiment, the light sources 502, 504 are arranged in an alternating pattern, with each first light source 502 bordered by two second light sources 504 and vice versa. The first light sources 502 generate beams having a first profile. The second light sources 504 generate beams having a second profile. The first and second profiles are different. The first and second beam profiles are overlapped to produce a uniform sheet of light. The number of light sources 502, 504 included in the illuminator 500 depends on the surface area to be illuminated. The larger the surface area, the higher the number of light sources 502, 504 needed to illuminate the surface. In one example, 16 of the first light sources 502 and 16 of the second light sources 504 are sufficient to form a uniform sheet of light across an end face of a typical honeycomb structure.

Figure 5B:
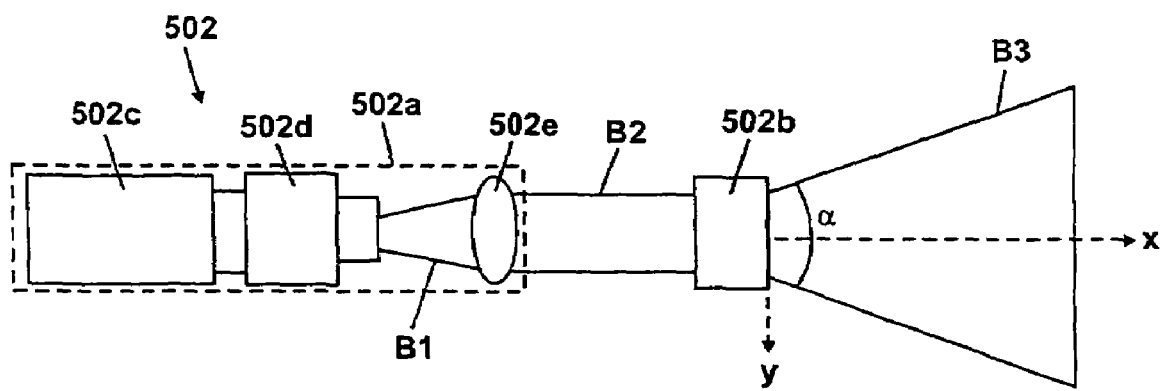
FIG. 5B is a schematic of a laser line generator.

In one embodiment, the first light sources 502 are laser line generators which generate beams having a linear profile. The laser line generators 502 include laser diode modules 502a and line generator modules 502b. FIG. 5B shows a possible configuration of the laser line generator 502. The laser diode module 502a includes a laser diode controller 502c, a laser diode 502d, and a collimating lens 502e. The laser diode controller 502c controls the laser diode 502d to produce diverging beam B1. The collimating lens 502 produces a collimated beam B2 from the diverging beam B1. The beam B2 enters the line generator module 502b, which includes one or more optical elements, such as a cylindrical lens, for converting the collimated beam B2 to a line beam B3. The line beam B2 spreads into a fan in a direction away from the line generator module 502b. The fan angle, α, is typically greater than 30°, preferably greater than 60°, more preferably equal to or greater than 90°.

Figure 6A:
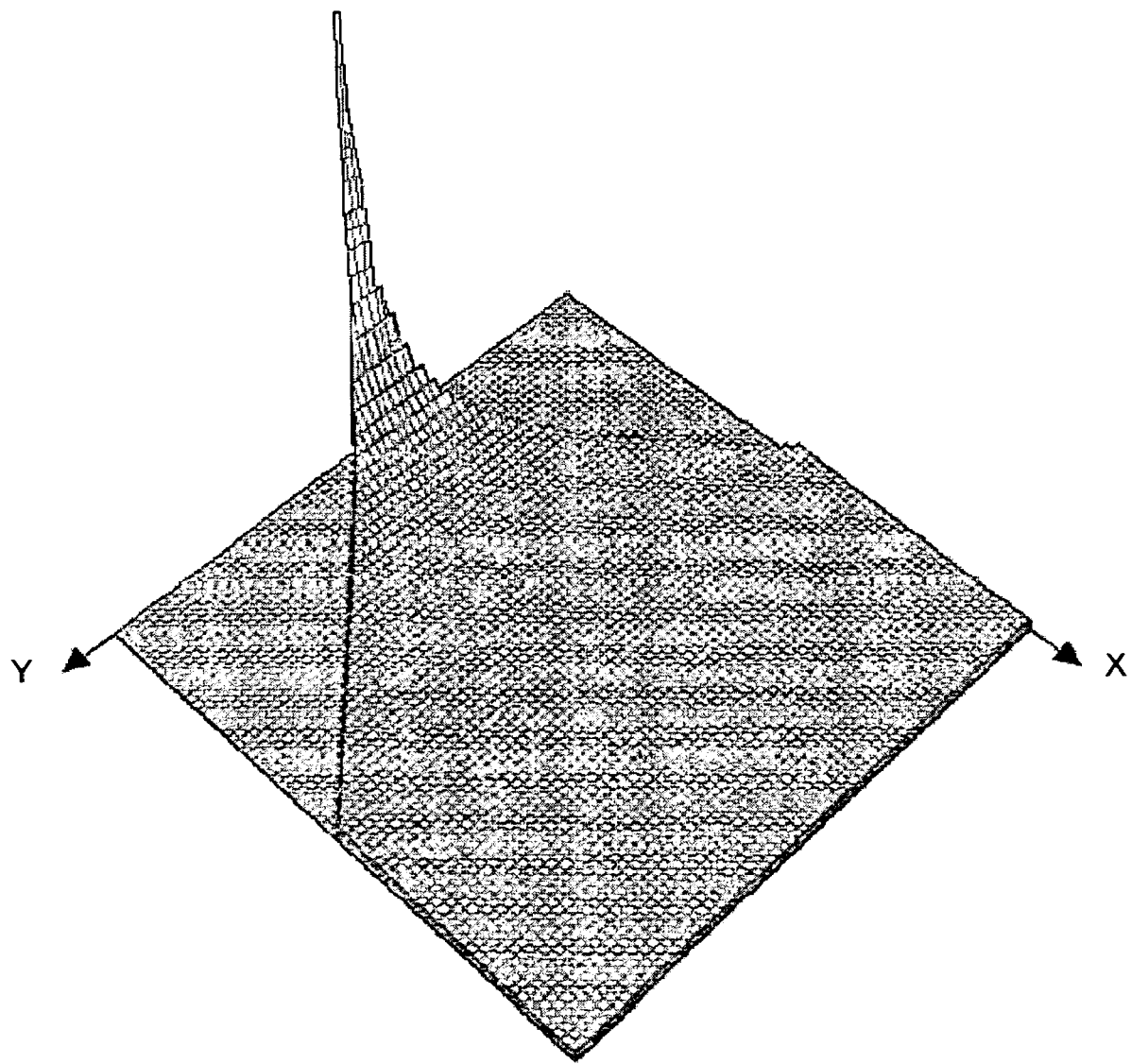
FIG. 6A shows a linear light distribution generated by a linear laser line generator.
Figure 6B:
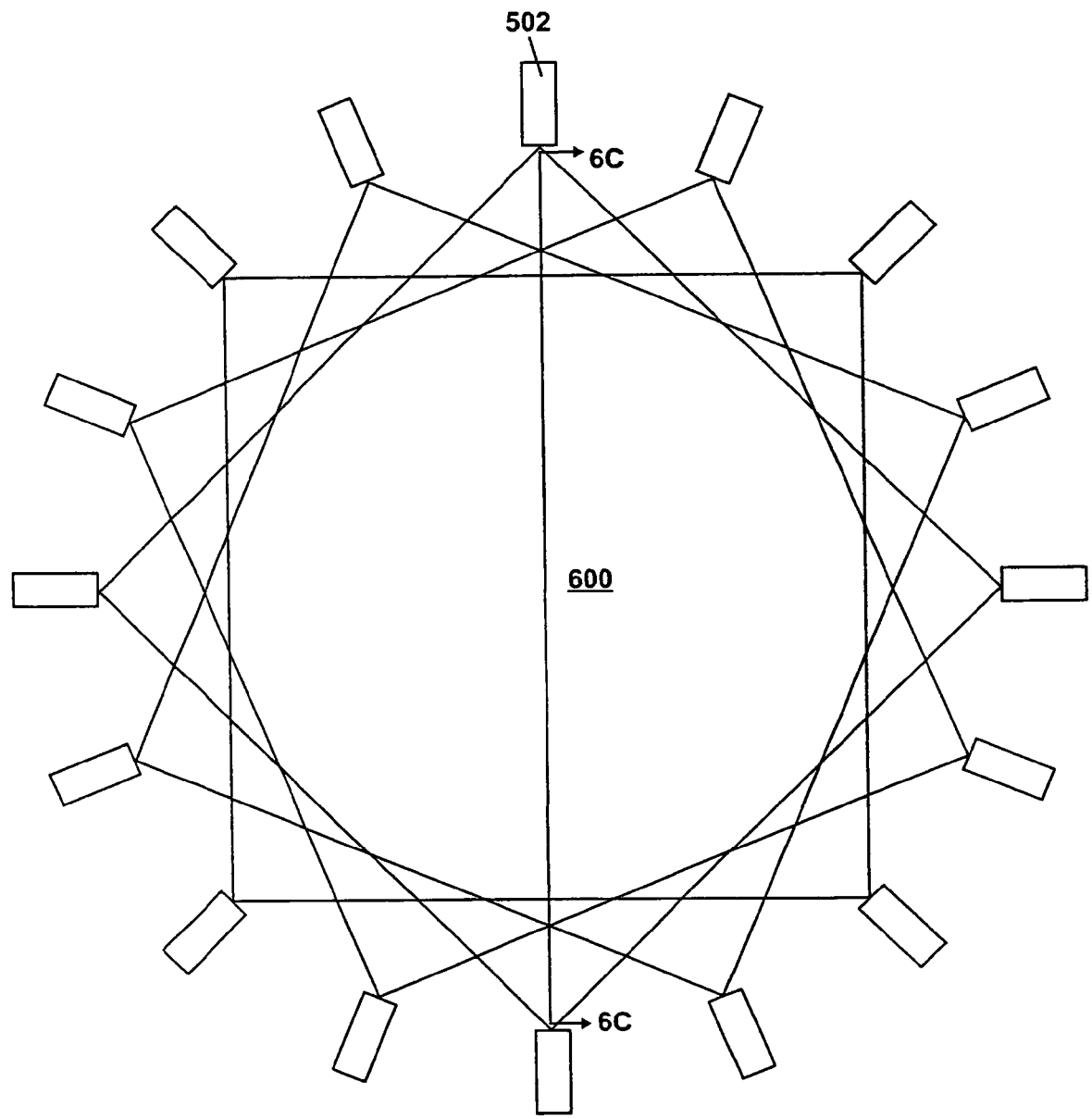
FIG. 6B shows illumination produced by 16 linear laser line generators arranged in a ring pattern.
Figure 6C:
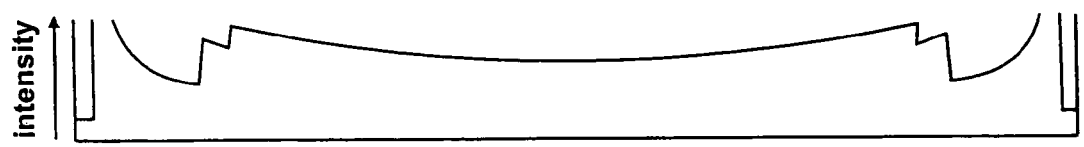
FIG. 6C shows intensity profile through the center of the illumination shown in FIG. 6B.

FIG. 6A shows a linear light distribution generated by a model calculating the intensity of the illumination generated by the laser line generator (502 in FIG. 5B) as it projects light in the x direction. The high point represents the energy density at the end of the line generator module (502b in FIG. 5B). In a direction away from the line generator module, the energy density decreases as well as spreads to form a fan. As the fan widens, the energy density decreases evenly. FIG. 6B shows illumination area 600 formed by 16 linear laser line generators 502 arranged in a ring pattern. FIG. 6C shows the intensity profile through the center of the illumination area. There is about 28% intensity variation across the illumination area. The energy density is less in the center than on the periphery of the illumination area.

Figure 7A:
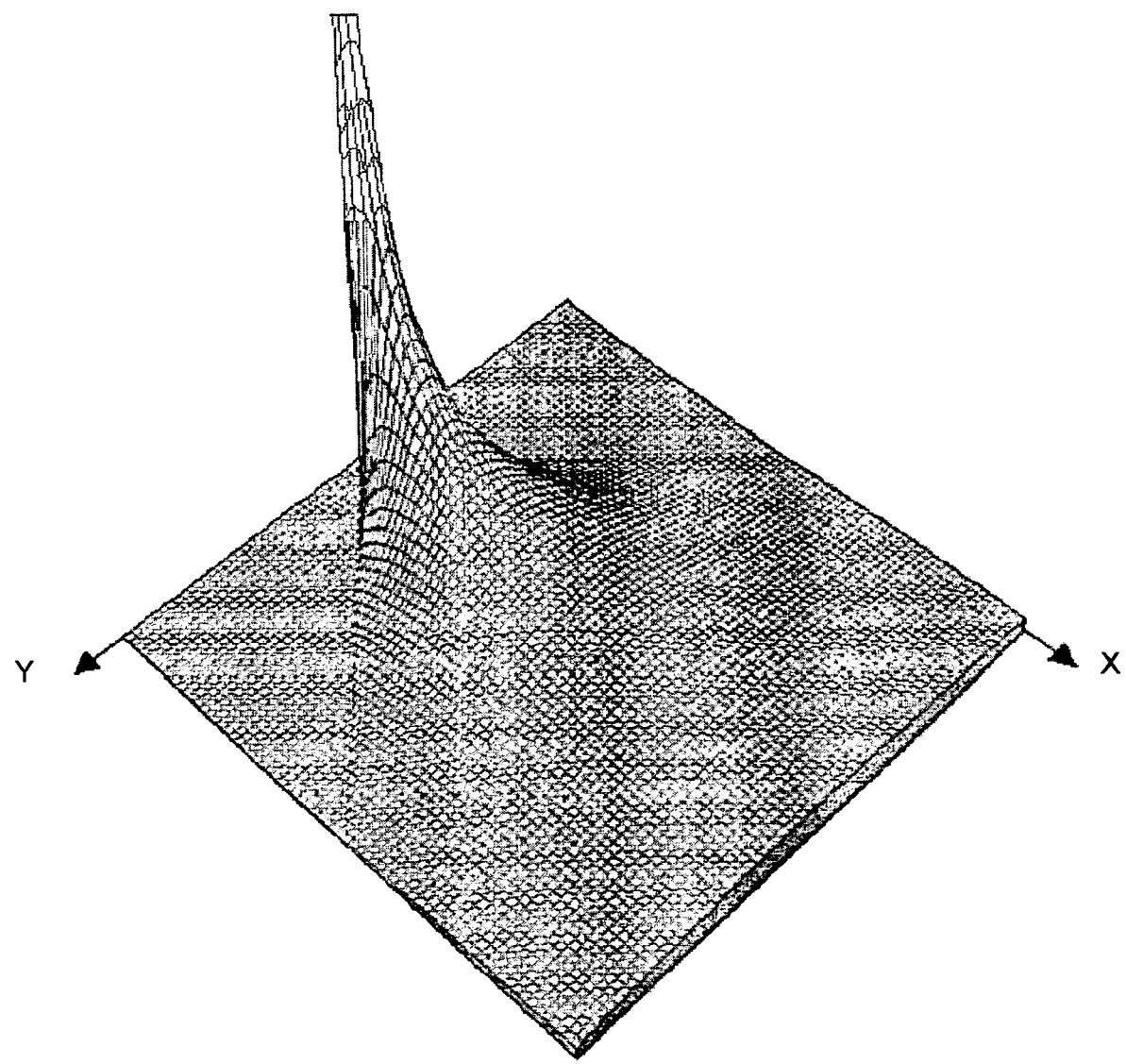
FIG. 7A shows a Gaussian light distribution generated by a Gaussian laser line generator.
Figure 7B:
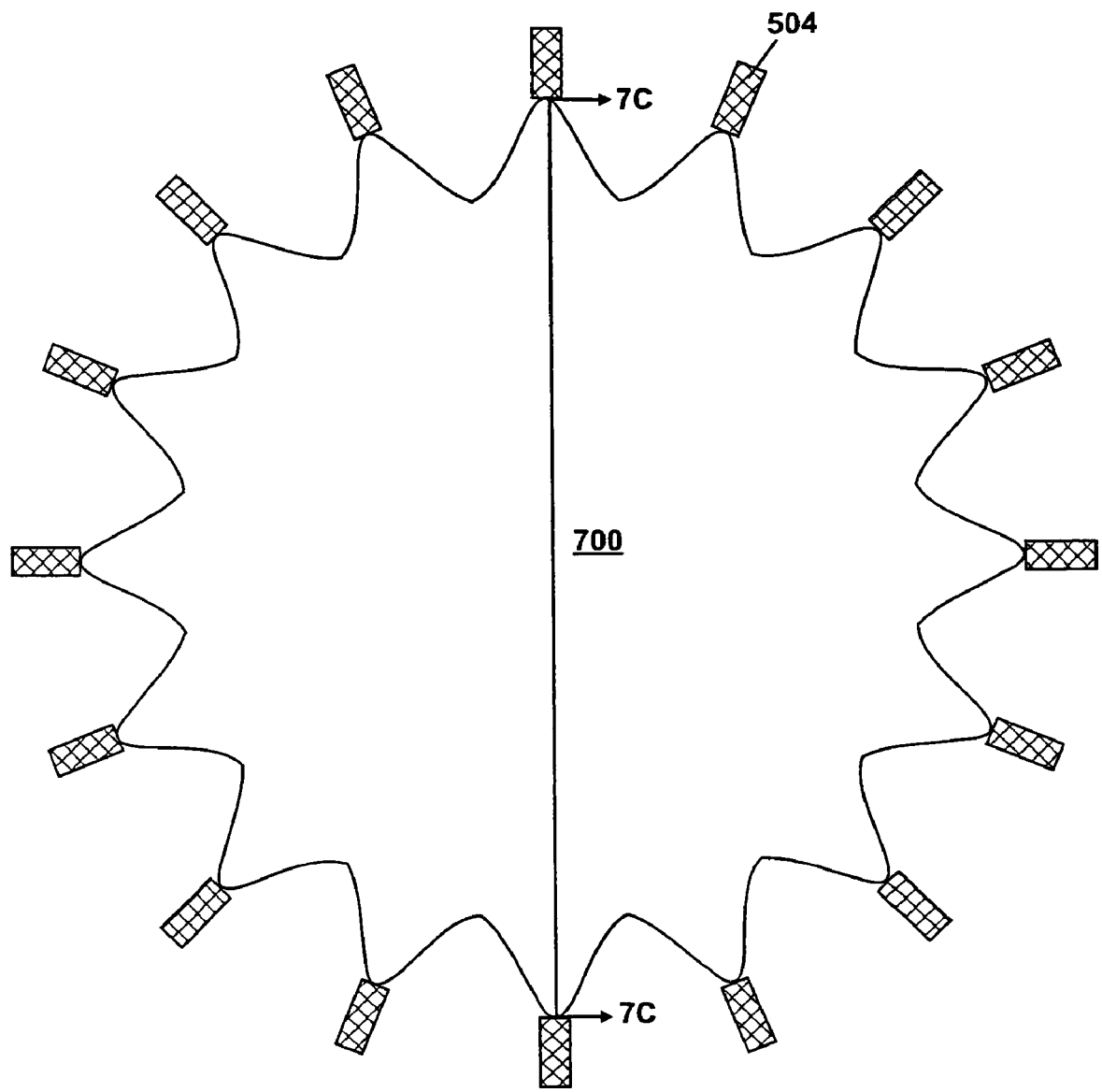
FIG. 7B shows illumination produced by 16 Gaussian laser line generators arranged in a ring pattern.
Figure 7C:
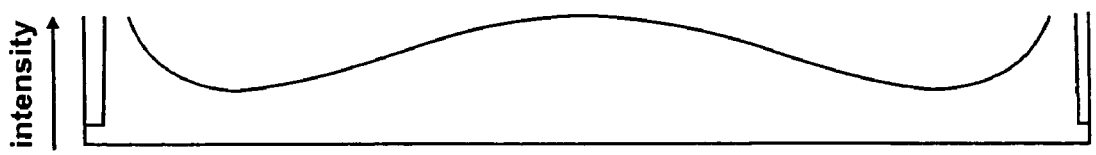
FIG. 7C shows intensity profile through the center of the illumination shown in FIG. 7B.

Returning to FIG. 5A, in one embodiment, the second light sources 504 are laser line generators which generate beams having a Gaussian profile. The laser line generators 504 include laser diodes 504a and line generator modules 504b. The laser line generators 504 are similar to the laser line generators 502 except that the line generator modules 504b generate a line beam having a Gaussian profile rather than a beam having a linear profile. FIG. 7A shows a Gaussian light distribution generated by a model calculating the intensity of the illumination generated by a laser line generator (504 in FIG. 5) as it projects in the x direction. The intensity of the light decreases as it moves in the positive x direction because it spreads out in a fan expanding in the y direction. The light intensity is highest in the center of the fan and tapers off in a Gaussian manner towards the edges of the fan. FIG. 7B shows illumination area 700 produced by 16 Gaussian laser line generators 504 arranged in a ring pattern. FIG. 7C shows the intensity profile through the center of the illumination area (700 in FIG. 7B). There is about 60% intensity variation across the illumination area (700 in FIG. 7B). The energy density is much greater in the center than on the periphery of the illumination area.

Figure 8A:
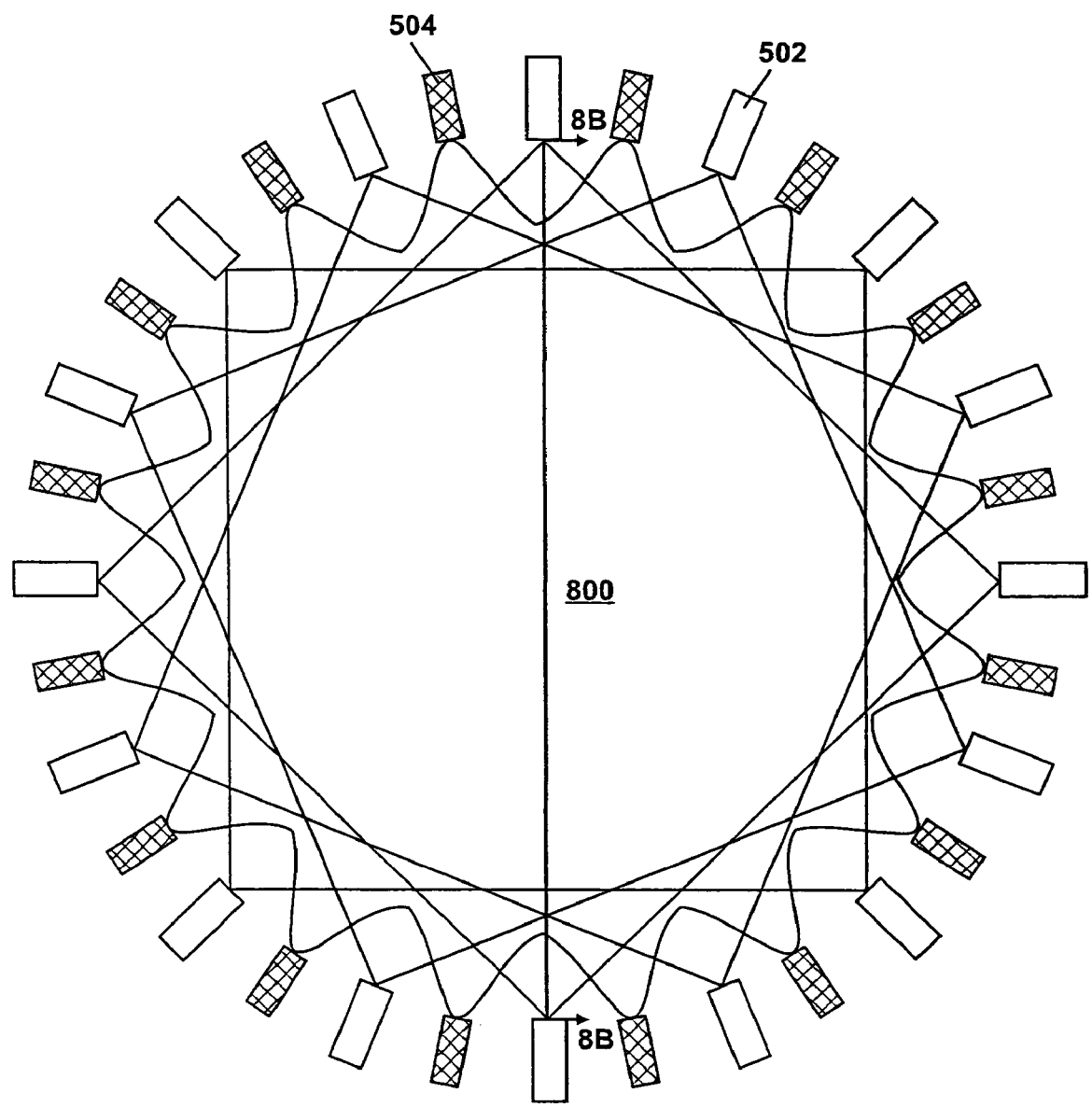
FIG. 8A shows a uniform sheet of light formed by overlapping the sheet of light formed by linear laser line generators with the sheet of light formed by Gaussian laser line generators according to an embodiment of the invention.
Figure 8B:
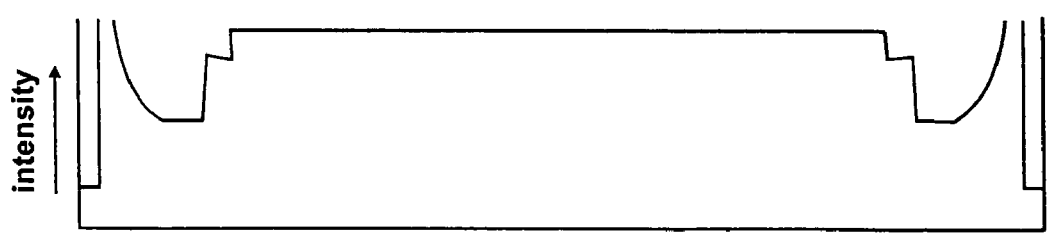
FIG. 8B shows the intensity profile through the center of the sheet of light shown in FIG. 8A.

From the foregoing, an illuminator consisting of only linear laser line generators would produce a sheet of light having energy density that is higher at the periphery than on the center. Also, an illuminator consisting of only Gaussian laser line generators would produce a sheet of light having energy density that is higher at the center than at the periphery. In accordance with one embodiment of the invention, the linear light distributions produced by the linear laser line generators can be combined with the Gaussian light distributions produced by the Gaussian laser line generators to achieve a uniform sheet of light. As an example, FIG. 8A shows an illumination area 800 formed by overlapping line beams from linear laser line generators 502 with line beams from Gaussian laser line generators 504. The linear and Gaussian laser line generators 502, 504 are arranged in a ring and alternating pattern as previously described. FIG. 8B shows the intensity profile through the center of the illumination area (800 in FIG. 8A). For an illuminator consisting of 16 linear laser line generators and 16 Gaussian laser line generators, there is about 2% maximum intensity variation across the illumination area. In general, the number of laser line generators and the laser line generator parameters can be suitably selected to achieve the desired intensity variation across the illumination area.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method of detecting defects in a plugged honeycomb structure, comprising the steps of:
   forming a sheet of light having a first color across a first end face of the honeycomb structure;
   generating a first reflected signal from the sheet of light at a location corresponding to a cell containing a defect in the honeycomb structure;
   illuminating the first end face with an incident light beam having a second color;
   generating a second reflected signal from the incident light beam; and
   capturing an image of the first and second reflected signals.

2. The method of claim 1 wherein generating the first reflected signal comprises passing a gaseous material into the honeycomb structure though a second end face of the honeycomb structure, wherein particles of the gaseous material emerge at the first end face though the cell containing the defect and intersect the sheet of light to produce the first reflected signal.

3. The method of claim 1 wherein the image is composed of the first color and the second color.

4. The method of claim 3 wherein the first color represents the size and location of the defect.

5. The method of claim 3 wherein the second color represents a configuration of cells at the first end face.

6. The method of claim 1 wherein the first and second colors are selected from the group consisting of red, green, and blue.

7. The method of claim 1 wherein capturing an image of the first and second reflected signals comprises sensing the first and second reflected signals using a charge-coupled device array.

8. The method of claim 1 further comprising processing the image to identify the cell in the honeycomb structure containing the defect.

9. The method of claim 8 further comprising marking or repairing the cell containing the defect.

10. The method of claim 1 wherein forming a sheet of light comprises generating a plurality of beams having a first profile and a plurality of beams having a second profile and overlapping the beams to form the sheet of light.

11. A system for detecting defects in a plugged honeycomb structure, comprising:
    a holder which supports the honeycomb structure;
    a first illuminator which forms a sheet of light having a first color across a first end face of the honeycomb structure;
    a second illuminator which illuminates the first end face with an incident light beam having a second color;
    a gas source which directs a gaseous material containing particulates at a second end face of the honeycomb structure; and
    an imaging device which captures an image of reflected signals produced from the sheet of light and the incident light beam.

12. The system of claim 11 wherein the imaging device comprises a charge-coupled device array for detecting the reflected signals.

13. The system of claim 11 further comprising a processor which receives the image from the imaging device and processes the image to identify cells in the honeycomb structure containing defects.

14. The system of claim 11 wherein the first illuminator comprises a plurality of first light sources having a first beam profile and a plurality of second light sources having a second beam profile, the first beam profile being different from the second beam profile.

15. The system of claim 14 wherein the first and second light sources are arranged in an alternating pattern.

* * * * *

UNITED STATES PATENT AND TRADEMARK OFFICE
CERTIFICATE OF CORRECTION

PATENT NO. : 7,520,918 B2 Page 1 of 1
APPLICATION NO. : 11/303532
DATED : April 21, 2009
INVENTOR(S) : Leon Robert Zoeller, III It is certified that error appears in the above-identified patent and that said Letters Patent is hereby corrected as shown below:

| Col. | Line | Description |
|------|------|-------------|
| 11 | 16 | "though" should be -- through --. |
| 11 | 18 | "though" should be -- through --. |

Signed and Sealed this

Twenty-eighth Day of July, 2009

JOHN DOLL
*Acting Director of the United States Patent and Trademark Office*